(12) United States Patent
Walter et al.

(10) Patent No.: US 8,274,562 B2
(45) Date of Patent: Sep. 25, 2012

(54) METHOD FOR IDENTIFYING SOILING ON A TRANSPARENT SCREEN

(75) Inventors: Michael Walter, Neuravensburg (DE); Matthias Zobel, Wasserburg (DE)

(73) Assignee: ADC Automotive Distance Control Systems GmbH, Lindau (DE)

( * ) Notice: Subject to any disclaimer, the term of this patent is extended or adjusted under 35 U.S.C. 154(b) by 1282 days.

(21) Appl. No.: 11/989,349

(22) PCT Filed: Feb. 21, 2006

(86) PCT No.: PCT/DE2006/000310
§ 371 (c)(1),
(2), (4) Date: Jan. 23, 2008

(87) PCT Pub. No.: WO2007/012299
PCT Pub. Date: Feb. 1, 2007

(65) Prior Publication Data
US 2009/0046148 A1 Feb. 19, 2009

(30) Foreign Application Priority Data
Jul. 27, 2005 (DE) .......... 10 2005 035 812

(51) Int. Cl.
*H04N 7/18* (2006.01)
(52) U.S. Cl. ........ 348/148; 348/113; 348/114; 348/115; 348/116; 348/117; 348/118; 348/149; 348/122; 382/104
(58) Field of Classification Search .......... 348/113–118, 348/148–149, 122; 382/104
See application file for complete search history.

(56) References Cited

U.S. PATENT DOCUMENTS

| | | | |
|---|---|---|---|
| 5,987,152 A * | 11/1999 | Weisser | 382/104 |
| 6,331,819 B1 | 12/2001 | Hog | |
| 6,376,824 B1 | 4/2002 | Michenfelder et al. | |
| 6,392,218 B1 * | 5/2002 | Kuehnle | 250/208.1 |
| 6,555,804 B1 | 4/2003 | Blasing | |
| 6,614,015 B1 | 9/2003 | Ba et al. | |
| 6,841,767 B2 | 1/2005 | Mindl et al. | |
| 2003/0201380 A1* | 10/2003 | Ockerse et al. | 250/208.1 |
| 2004/0004456 A1 | 1/2004 | LeBa et al. | |
| 2008/0027607 A1* | 1/2008 | Ertl et al. | 701/36 |

FOREIGN PATENT DOCUMENTS

| | | |
|---|---|---|
| DE | 195 04 606 | 8/1996 |
| DE | 197 00 665 | 7/1997 |
| DE | 197 04 818 | 8/1997 |
| DE | 197 40 364 | 3/1999 |
| DE | 197 49 331 | 5/1999 |
| DE | 198 39 273 | 9/1999 |
| DE | 199 09 987 | 9/2000 |
| DE | 102 30 200 | 1/2004 |
| DE | 103 03 046 | 10/2004 |
| DE | 103 16 794 | 11/2004 |
| DE | 103 22 010 | 12/2004 |
| EP | 0 832 798 | 4/1998 |

* cited by examiner

*Primary Examiner* — Wing Chen
*Assistant Examiner* — Benjamin M Thieu
(74) *Attorney, Agent, or Firm* — W. F. Fasse

(57) ABSTRACT

A camera for identifying soiling on a protective screen, such as a vehicle windscreen, is focused on a scene through the protective screen and can be used to identify soiling and for other applications, e.g. to identify driving lanes and/or objects in the scene. Soiling is identified merely by evaluating successively recorded image frames, and artificial reference frames or reference objects are not required. A prerequisite is that the relative speed $v_{rel}$ between the camera and at least one recorded object in the scene is not equal to zero and its trajectory in the image is predicted. By comparing the relevant image frame sections, possible soiling on subregions of the protective screen is identified.

20 Claims, 1 Drawing Sheet

METHOD FOR IDENTIFYING SOILING ON A TRANSPARENT SCREEN

FIELD OF THE INVENTION

The present invention relates to a method for identifying soiling on a protective screen. This invention is used e.g. in motor vehicles. Camera sensors are used here to an increased extent to record the surroundings, in particular to identify driving lanes and/or to identify objects, with a view to the driving direction or to the backward region. The camera sensors are usually attached in the interior of the vehicle behind a windscreen. A faultless function of the sensor is ensured only if the view is not masked by foreign objects on the screen.

BACKGROUND INFORMATION

Numerous methods for measuring soiling of screens e.g. in motor vehicles are known. In DE 10230200 a detector is described to identify objects on a surface of a transparent element. In this case, the detector is at least approximately focused on the surface and for identifying soiling the contrast distribution of the recorded frames is evaluated. A further method to identify objects located on a windscreen is shown in DE 19749331. For this purpose, a sensor array is focused on the exterior of the windscreen. An analysis of the spatial frequencies in the recorded frame provides information on a soiling of the windscreen. Due to the focusing of the camera on the surface both arrangements cannot be used for other camera-based applications, e.g. for coverage of the surroundings. In DE 19700665 a camera-based sensor is described, which detects foreign materials on a transparent screen. For this purpose the image of a firmly installed light emitting reference object is recorded through the screen and is compared with a reference image. It is disadvantageous with this arrangement that a reference object is needed to measure soiling.

SUMMARY OF THE INVENTION

It is the object of the invention to economically identify soiling of a protective screen in the field of view of a camera, which is used also for other applications in particular for coverage of the surroundings.

In accordance with the invention this object is achieved by a passive camera-based approach. For this purpose, a camera is provided, which is focused on the surroundings behind a transparent screen. It is advantageous with this arrangement that the camera can be used to identify soiling and to cover, i.e. monitor or record the surroundings. In a given cycle, frames or successive images are read out from the camera, e.g. at a rate of 25 frames/s. The recorded image frames are evaluated in terms of soiling on the protective screen. Thus, no further artificial reference frames or reference objects are needed, so that for the user no further costs and/or adjustment expenditure arise here. Soiling can only be identified according to the presented method, if the relative velocity $v_{rel}$ of the camera and of at least one object recorded in the surroundings is not equal to zero. This is ensured in an application e.g. in the motor vehicle by intrinsic speed of the vehicle $V_{vehicle} > 0$ m/s. Thus, the relative velocity towards static objects in the vehicle surroundings is $v_{rel} > 0$ m/s. Objects with $v_{rel} > 0$ m/s continuously change their position in relation to the camera and thus also their position in the frame. The calculated process of this movement in the frame is called a trajectory in the following description. This means that the same object is depicted chronologically offset in different frame sections. Now if a frame section is totally or partly masked by soiling, then the object is changed or not depicted at all. By comparing the frame sections, possible soiling on subregions of the protective screen is identified. In order to select the frame sections suitable for the comparison, the trajectory of at least one object with $v_{rel} > 0$ is predicted.

In an advantageous embodiment of the invention measuring windows are set along the predicted trajectory of objects, so that the same object is depicted successively in the different measuring windows with a suitable read-out frequency and/or a suitable number of averagings of a measurement. The same applies for several similar objects, in particular for road markings, along a predicted trajectory. The latter, too, are visible in the measuring windows along their trajectory with a suitable read-out frequency and/or a suitable number of averagings of a measurement. If the illustration range of a measuring window is masked by soiling, the object is changed or not recorded at all in this measuring window. From the comparison of the object illustrations in corresponding measuring windows soiling in subregions of the protective screen is identified. Measuring windows along a predicted trajectory are called here corresponding measuring windows, in which an object illustration is expected according to the prediction.

In an advantageous arrangement of the invention in a measuring window the contrast is evaluated and/or the average value of the brightness is determined. The average value is not always sufficient to identify soiling. Shadows e.g. of vehicles, trees, buildings etc. can result in a local change of the brightness. However, if the average value and the standard deviation of the brightness are taken into consideration, it is possible to make a conclusion, since a shadow in front of the camera causes a local change of the average value, however, it does not lead to a substantial change of the standard deviation within the measuring window. The gray tone differences can be evaluated in addition to the other values or exclusively. If the difference of the determined values in corresponding measuring windows exceeds a threshold value, soiling is identified.

In case of a linear movement of the camera itself, the trajectories of static objects within the imaging range of the camera run along straight lines, which proceed radially from the vanishing point of the image or the field of view. In a preferred form of embodiment, measuring windows are set along the cited straight lines. In case of a non-linear movement of the camera itself or of a non-linear movement to be expected, in an advantageous embodiment of the invention the trajectory of objects is calculated based on the characteristics of the surroundings and/or the instantaneous camera movement and/or the mounting position of the camera. If, for example, the camera is used to measure soiling in a motor vehicle, an object trajectory, in particular that of a static object, can be calculated from the estimated driving lane parameters such as curvature and offset, the mounting position of the camera, its height, angle of pitching, yawing and roll, as well as from the intrinsic camera parameters, the focal length, perspective center point, etc. If there are no driving lane parameters available, because the system is not able to estimate a driving lane due to soiling or a lack of road markings, then the curvature can be determined on the basis of the steering angle. The measuring windows are arranged along the predicted trajectory.

An advantageous embodiment of the invention is a motor vehicle with a camera for observing the surroundings, e.g. to identify driving lanes and/or objects with a view to the driving direction or to the backward region, and to measure soiling.

BRIEF DESCRIPTION OF THE DRAWINGS

Further advantages and characteristics of the invention are described in detail by way of examples on the basis of one example of embodiment and of two illustrations, in which.

DETAILED DESCRIPTION OF AN EXAMPLE EMBODIMENT OF THE INVENTION

Figure 1:
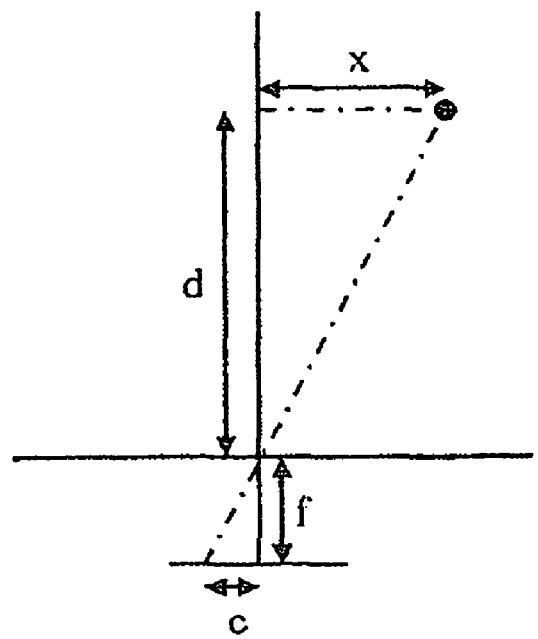
FIG. 1: shows a determination of the column c of a measuring window placed in a line or row y with lateral offset x.

The example embodiment describes a motor vehicle with a camera to identify soiling on a protective screen. The camera is focused on the surroundings in front of the vehicle and not on the protective screen and is used for coverage of the surroundings. The vehicle moves in a temporal average on a straight line. Static objects in the surroundings thus move, within the imaging range of the camera, on straight lines, which proceed radially from the vanishing point of the image or the field of view. Naturally, this applies also to the median strip and to the side limits of a road, the course of the roadway and oncoming vehicles. If measuring windows are positioned along the radially running straight lines, under ideal conditions, i.e. no damping or soiling, in the corresponding measuring windows, e.g. in the imaging range of the median strip or the roadway, it is to be expected that there will be identical contrasts, average values, standard deviations and gray tone differences. If disturbances (soiling) are present in the close range of the camera, they can be identified on the basis of local discontinuities. In the simplest case a disturbance can be identified on the basis of the differences between the measured values averaged along the radials and the measured values chronologically averaged in the measuring windows. If the difference exceeds a threshold it can be assumed that the associated measuring window is masked by soiling. The strength of the discontinuity depends on the roadway textures, the degree of soiling, the lighting, as well as on the size of the measuring windows.

However, also non-static objects with a relative velocity not equal to zero, e.g. oncoming vehicles can be used to measure soiling. Also these objects move within the illustration range of the camera on radials, which proceed from the vanishing point of the frame. The measuring windows are set along the radials, so that the object is depicted in all measuring windows along the given radials within a time period Δt with a suitable read-out frequency and/or a suitable chronological averaging of the measured values. Also in this case soiling will be identified on the basis of discontinuities.

As already represented above, the camera can also be used for coverage, i.e. monitoring or recording of the surroundings. If the vehicle is equipped with a surroundings detection system, the course of the driving lane and the associated markings can be calculated in advance. The measuring windows are set along the lane. For this purpose, at first the camera picture is divided into N×M regions. For each pre-calculated object trajectory the regions lying closest are determined and are set as measuring windows. If no marking is found in a predicted measuring window, a counter z(n, m) is incremented. If a marking is found in a predicted measuring window, a counter z(n, m) is reset. If a counter z(n, m) exceeds a fixed or a speed-dependent threshold, the region (n, m) is classified as soiled.

In order to determine the size and the position of the measuring windows in the image frame, the roadway or traveling lane can be divided into regions of equidistant width. The size and the position of the measuring windows in the image frame result from the imaging model of the camera. FIG. 1 represents the simplest case of a camera directed downwards. The column c of a measuring window located in a line or row y with lateral offset x is calculated according to $$c = \frac{x \cdot f}{d \cdot \eta}.$$

Figure 2:
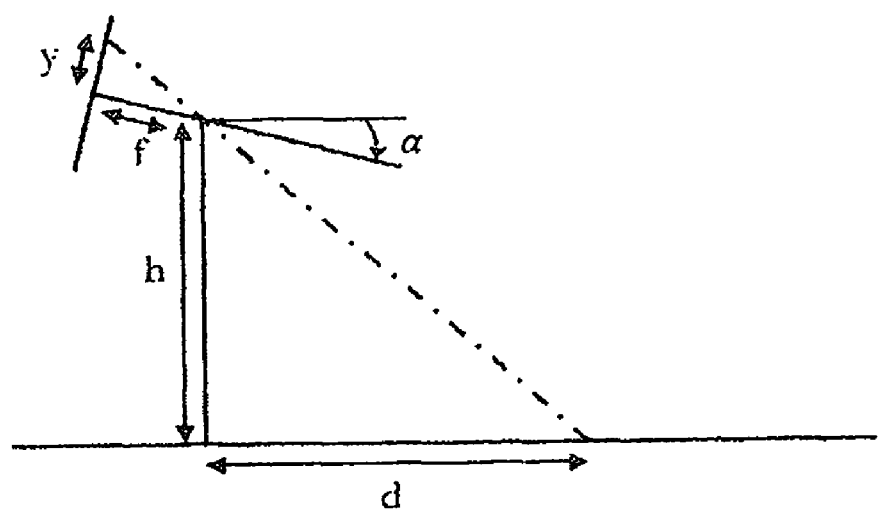
FIG. 2: shows a determination of the distance of a point d to the camera.

Here d is the distance of a point from the camera, c the image frame column of the point, $\eta$ the pixel size and f the camera focal length. FIG. 2 shows the distance determination of a point d to the camera. The distance is determined from h the camera mounting height, a the camera pitch angle, y the image frame line or row of the point, $\eta$ the pixel size and f the camera focal length, according to $$d = h \cdot \frac{1 - t \cdot \tan\alpha}{t + \tan\alpha} \text{ with } t = y \cdot \frac{\eta}{f}$$

The invention claimed is:

1. A method to identify soiling on a protective screen of a motor vehicle, wherein a camera is arranged in the motor vehicle to monitor, through the protective screen, a surrounding environment outside of the motor vehicle, and the camera is focused on a scene in the surrounding environment through the protective screen, characterized in that a relative velocity $v_{rel}$ between the camera and at least one recorded object in the surrounding environment recorded by the camera is not equal to zero, a trajectory of the at least one recorded object with $v_{rel}$ not equal to zero is predicted, and a degree of correspondence of the recorded object and/or several similar objects as recorded in different image regions respectively imaged by the camera through different partial areas of the protective screen is analyzed and a conclusion is derived therefrom about soiling on the screen based on determining a difference of a degree of soiling respectively on the different partial areas of the protective screen.

2. A method according to claim 1, characterized in that measuring windows are set along the predicted trajectory, the recorded object is detected in more than one measuring window in images recorded in a chronologically offset manner and/or several similar objects, being roadway markings, along the predicted trajectory are detected in more than one measuring window.

3. A method according to claim 2, characterized in that in case of a linear movement of the camera, with a linear movement of the vehicle, the measuring windows are set along straight lines, which proceed radially from a vanishing point of a respective camera image.

4. A method according to claim 1, characterized in that in a measuring window respective values of an image contrast and/or an image brightness or its standard deviation and/or gray tone differences are determined, and soiling is identified, if a difference of the values in corresponding measuring windows is greater than a given threshold value.

5. A method according to claim 4, characterized in that in case of a linear movement of the camera, with a linear movement of the vehicle, the measuring windows are set along straight lines, which proceed radially from a vanishing point of a respective camera image.

6. A method according to claim 1, characterized in that the trajectories of the recorded objects, which are static objects, are predicted on the basis of
   a) characteristics of the surrounding environment and/or
   b) an instantaneous camera movement of the camera and/or
   c) a mounting position of the camera
and the measuring windows are arranged along at least one of the trajectories.

7. A method of identifying soiling on a protective screen of a motor vehicle using a camera arranged in the vehicle, comprising steps:
   a) directing and focusing a field of view of said camera through said protective screen so as to acquire successive image frames of a surrounding environment outside of said motor vehicle with said camera;
   b) selecting at least one selected object that is present in said surrounding environment, and that is imaged respectively as at least one object image in said successive image frames, and that has a non-zero relative velocity relative to said camera such that said at least one object image is moving in said field of view and is imaged successively through different sub-regions of said protective screen in said successive image frames;
   c) predicting a respective trajectory of a motion of said at least one object image in said field of view;
   d) specifying plural image regions, corresponding to said sub-regions of said protective screen, respectively along said trajectory in said field of view among said successive image frames such that said at least one object image respectively appears successively in said plural image regions successively among said successive image frames;
   e) detecting respective values of at least one image parameter of said at least one object image successively in said plural image regions successively among said successive image frames; and
   f) comparing said respective values in said plural image regions successively among said successive image frames, and determining a variation of a degree of soiling of said different sub-regions of said protective screen from said comparing.

8. The method according to claim 7, wherein said field of view of said camera is focused only on said surrounding environment and is not focused on said protective screen.

9. The method according to claim 7, wherein said at least one image parameter comprises at least one of: an image contrast, image gray tone variations, an average value of image brightness, and a standard deviation of image brightness.

10. A method of identifying soiling on a protective screen of a motor vehicle using a camera arranged in the vehicle, comprising steps:
   a) acquiring with said camera, through said protective screen, successive image frames of a surrounding environment outside of said motor vehicle;
   b) selecting at least one object of said surrounding environment, wherein each said object exhibits motion among said successive image frames;
   c) predicting a respective trajectory of said motion of each said object among said successive image frames;
   d) detecting respective values of at least one image parameter of each said object respectively at successive positions of said object along said trajectory through successive different sub-regions of said protective screen respectively in said successive image frames; and
   e) evaluating a variation of said values, and determining different degrees of soiling of said different sub-regions of said protective screen from a result of said evaluating.

11. The method according to claim 10, wherein, for said acquiring of said image frames, said step a) comprises focusing said camera on said surrounding environment and not on said protective screen.

12. The method according to claim 10, wherein said at least one image parameter comprises at least one of: an image contrast, image gray tone variations, an average value of image brightness, and a standard deviation of image brightness.

13. The method according to claim 10, further comprising comparing said different degrees of soiling to a threshold, and determining that an unacceptable degree of soiling exists when at least one of said different degrees of soiling exceeds said threshold.

14. The method according to claim 10, further comprising establishing measuring windows along said trajectory in a field of view of said camera, wherein said successive positions respectively fall into successive ones of said measuring windows, wherein said successive measuring windows correspond to said different sub-regions of said protective screen, and wherein said detecting is carried out successively in said successive measuring windows.

15. The method according to claim 14, wherein said measuring windows are established along straight radial lines extending radially outwardly from a vanishing point of said field of view of said camera.

16. The method according to claim 10, wherein said respective trajectory for each said object is established along a straight radial line extending radially outwardly from a vanishing point of each one of said image frames.

17. The method according to claim 10, wherein said object is a static object that does not move in said surrounding environment, said vehicle is moving in said surrounding environment, and said trajectory of said static object is predicted based on at least one of: characteristics of said surrounding environment, an instantaneous camera motion of said camera, and a mounting position of said camera on said motor vehicle.

18. The method according to claim 10, wherein said at least one object comprises successive similar objects being roadway markings in said surrounding environment.

19. The method according to claim 10, wherein said protective screen is a windshield of said motor vehicle.

20. The method according to claim 10, further in combination with using said camera to monitor said surrounding environment, comprising obtaining from said successive image frames additional information, in addition to said selecting, said predicting and said detecting of said steps b), c) and d), and using said additional information in an additional application in said motor vehicle.

* * * * *